United States Patent
Camacho et al.

(10) Patent No.: US 10,369,151 B2
(45) Date of Patent: Aug. 6, 2019

(54) TREATMENT OR PREVENTION OF AUTISM DISORDERS USING MENTHOL, LINALOOL AND/OR ICILIN

(71) Applicant: NESTEC S.A., Vevey (CH)

(72) Inventors: Susana Camacho, Lausanne (CH); Stephanie Michlig Gonzalez, Le Mont-sur-Lausanne (CH); Johannes Le Coutre, Pully (CH); Henry Markram, Lausanne (CH); Maurizio Pezzoli, Lausanne (CH)

(73) Assignee: Societe des Produits Nestle S.A., Vevey (CH)

( * ) Notice: Subject to any disclaimer, the term of this patent is extended or adjusted under 35 U.S.C. 154(b) by 0 days.

(21) Appl. No.: 14/892,038

(22) PCT Filed: May 23, 2014

(86) PCT No.: PCT/EP2014/060642
§ 371 (c)(1),
(2) Date: Nov. 18, 2015

(87) PCT Pub. No.: WO2014/187946
PCT Pub. Date: Nov. 27, 2014

(65) Prior Publication Data
US 2016/0089370 A1    Mar. 31, 2016

Related U.S. Application Data

(60) Provisional application No. 61/827,229, filed on May 24, 2013.

(51) Int. Cl.
| | | |
|---|---|---|
| A61K 31/045 | (2006.01) | |
| A23L 1/30 | (2006.01) | |
| A61K 9/00 | (2006.01) | |
| A61K 31/513 | (2006.01) | |
| A23L 33/105 | (2016.01) | |

(52) U.S. Cl.
CPC .......... *A61K 31/513* (2013.01); *A23L 33/105* (2016.08); *A61K 9/0053* (2013.01); *A61K 31/045* (2013.01); *A23V 2002/00* (2013.01)

(58) Field of Classification Search
CPC .. A61K 31/513; A61K 9/0053; A61K 31/045; A23L 33/105; A23V 2002/00
See application file for complete search history.

(56) References Cited

U.S. PATENT DOCUMENTS

2011/0159048 A1* 6/2011 Crain .................. A61K 31/439
424/400

FOREIGN PATENT DOCUMENTS

| | | | |
|---|---|---|---|
| CN | 1728981 | | 2/2006 |
| CN | 102258751 | A | 11/2011 |
| JP | 09176031 | A | 7/1997 |
| JP | 2006199662 | A | 8/2006 |
| JP | 2011046659 | A | 3/2011 |
| JP | WO 2012160608 | A1 * | 11/2012 .......... A61K 36/752 |
| KR | 20120103317 | A | 9/2012 |
| WO | 2004056332 | | 7/2004 |
| WO | 2006029142 | | 3/2006 |

OTHER PUBLICATIONS

Menthol—Wikipedia.*
Assessment Report on Mentha X Piperita L., Folium, London, Sep. 4, 2008 (Year: 2008).*
Olmos-Serrano et al. "Defective GABAergic Neurotransmission and Pharmacological Rescue of Neuronal Hyperexcitability in the Amygdala in a Mouse Model of Fragile X Syndrome" The Journal of Neuroscience, 2010, vol. 30, No. 29, pp. 9929-9938.
Kleinhans et al. "Reduced Neural Habituation in the Amygdala and Social Impairments in Autism Spectrum Disorders" Am. J. Psychiatry, 2009, vol. 166, No. 4, pp. 467-475.
Kawasaki et al. "Inhibition by menthol and its related chemicals of compound action potentials in frog sciatic nerves" Life Sciences, 2013, vol. 92, pp. 359-367.
Chinese Office Action—Appl. No. 201480029048.3 dated May 2, 2017—4 pages (English translation).
Chinese Office Action—Appl. No. 201480029048.3 dated May 2, 2017—8 pages.
Andersson et al., "TRPM8 Activation by Menthol, Icilin, and Cold is Differentially Modulated by Intracellular pH," The Journal of Neuroscience, vol. 24, No. 23, Jun. 9, 2004, pp. 5364-5369.
Chuang et al., "The Super-Cooling Agent Icilin Reveals a Mechanism of Coincidence Detection by a Temperature-Sensitive TRP Channel", Neuron, vol. 43, Sep. 16, 2004, pp. 859-869.
Japanese Patent Office Communication for corresponding application No. P2016-514432, Dispatch No. 109252, Dispatch Date Mar. 13, 2018, 12 pages.
Wang et al., "Modern Psychologic Medicine", People's Military Medical Publisher, 1st edition, Sep. 2002, pp. 1132-1135.

* cited by examiner

Primary Examiner — Sarah Pihonak
Assistant Examiner — Jason Deck
(74) Attorney, Agent, or Firm — K&L Gates LLP

(57) ABSTRACT

Compositions for treatment or prevention of autism disorders are provided, and the compositions contain a therapeutically effective amount of a compound selected from the group consisting of Menthol, Linalool, Icilin and combinations thereof. Methods for treatment or prevention of autism disorders are also provided, and the methods include administering such compositions.

13 Claims, 5 Drawing Sheets

TREATMENT OR PREVENTION OF AUTISM DISORDERS USING MENTHOL, LINALOOL AND/OR ICILIN

CROSS REFERENCE TO RELATED APPLICATIONS

The present application is a National Stage of International Application No. PCT/EP2014/060642, filed on May 23, 2014, which claims priority to U.S. Provisional Application Ser. No. 61/827,229, filed on May 24, 2013, the entire contents of which are being incorporated herein by reference.

BACKGROUND

The present disclosure generally relates to methods and compositions for treatment or prevention of autism disorders. More specifically, the present disclosure relates to compositions comprising at least one of Menthol, Linalool or Icilin and further relates to methods comprising administering such compositions.

Autism disorders are severe neurobehavioral syndromes understood to be inherited disorders, although environmental factors are thought to contribute in at least some autism disorders. Autism disorders typically cause major defects in perception, cognition, executive functions and motor control. Although these effects differ between types of autism, abnormalities in language and social skills are pervasive throughout types of autism disorders.

The underlying mechanisms of autism disorders are poorly understood, but a hypothesis has gained favor that autism disrupts neural systems by causing an abnormal balance of the ratio of excitation to inhibition, possibly associated with chronically elevated neuronal activity without cell death. For example, Fragile X syndrome is a type of autism disorder arising from mutations in an untranslated region of the FMR1 gene on the X chromosome. This gene encodes a protein required for normal neural development, and the mutations prevent expression of this protein.

Because of the excessive glutaminergic mechanisms involved in autism, glutamate antagonists have been proposed as treatments for autism and have seen some positive developments. These antagonists inhibit the binding of glutamate to NMDA receptors such that accumulation of $Ca^{2+}$ and therefore excitotoxicity can be avoided. However, use of glutamate antagonists presents a huge obstacle because the treatment interferes with the normal action of glutamate under standard conditions. A number of glutamate antagonists have been explored as options in central nervous system (CNS) disorders, but many are found to lack efficacy or have intolerable side effects.

There is a clear and persisting need to prevent and treat autism disorders, such as fragile X syndrome for example.

SUMMARY

The present inventors surprisingly and unexpectedly found that several active compounds from spices can depress neural activity in the neocortex and the amygdale. These compounds are Menthol and Linanool which are transient receptor potential M8 (TRPM8) channel agonists. The present inventors discovered the same effect with Icilin, a synthetic super-agonist of the TRPM8 ion channel, even though the structure of Icilin is not related to Menthol.

Accordingly, in a general embodiment, the present disclosure provides a method for treating an autism disorder. The method comprises administering to an individual having the autism disorder a composition comprising a therapeutically effective amount of a compound selected from the group consisting of Menthol, Linalool, Icilin and combinations thereof.

In a related embodiment, the autism disorder is selected from the group consisting of classic autism, Asperger's syndrome, childhood disintegrative disorder, Rett syndrome, pervasive developmental disorders-not otherwise specified ("PDD-NOS"), fragile X syndrome, and combinations thereof.

In a related embodiment, the composition is selected from the group consisting of a medicament, a food product and a supplement to a food product.

In a related embodiment, the composition is administered periodically for at least one year.

In another embodiment, a method for preventing an autism disorder is provided. The method comprises administering to an individual in need thereof a composition comprising a therapeutically effective amount of a compound selected from the group consisting of menthol, linalool, icilin and combinations thereof.

In a related embodiment, the autism disorder is selected from the group consisting of classic autism, Asperger's syndrome, childhood disintegrative disorder, Rett syndrome, pervasive developmental disorders-not otherwise specified ("PDD-NOS"), fragile X syndrome, and combinations thereof.

In a related embodiment, the individual is an infant.

In a related embodiment, the individual is a young child.

In a related embodiment, the composition is administered periodically for at least one year. The composition can be administered daily.

In another embodiment, a composition for treating or preventing an autism disorder is provided. The composition comprises a therapeutically effective amount of a compound selected from the group consisting of Menthol, Linalool, Icilin and combinations thereof.

In a related embodiment, the composition is a medicament.

In a related embodiment, the composition is a food product. The food product can comprise a component selected from the group consisting of protein, carbohydrate, fat and combinations thereof.

In a related embodiment, the composition is a supplement to a food product.

An advantage of the present disclosure is to prevent or treat an autism disorder more effectively and/or more safely than glutamate antagonists.

Another advantage of the present disclosure is to prevent or treat an autism disorder without interfering with the normal action of glutamate under standard conditions.

Still another advantage of the present disclosure is to prevent or treat an autism disorder with compounds that can be easily and safely used in food products.

Yet another advantage of the present disclosure is to prevent or treat an autism disorder by targeting the pre-synaptic phase of neuronal firing.

An additional advantage of the present disclosure is to prevent or treat an autism disorder by targeting the pre-synaptic phase of neuronal firing while reducing the possibility of excitotoxicity.

Another advantage of the present disclosure is to prevent or treat an autism disorder with naturally-occurring compounds that can be found in spices.

Still another advantage of the present disclosure is to prevent or treat an autism disorder with tolerable side effects or no side effects.

Yet another advantage of the present disclosure is to prevent or treat fragile X syndrome.

Additional features and advantages are described herein, and will be apparent from, the following Detailed Description and the Figures.

DETAILED DESCRIPTION

Figure 1:
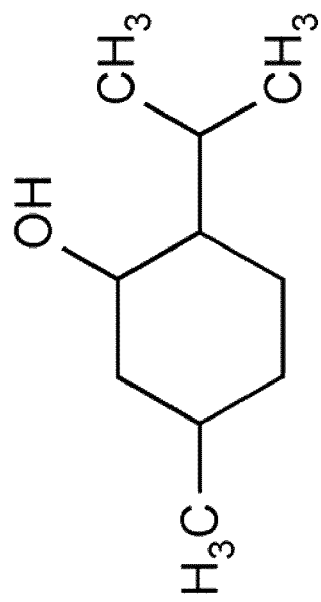
FIG. 1 shows the chemical structures of compounds that can be used in embodiments of the composition according to the present disclosure.
Figure 1:
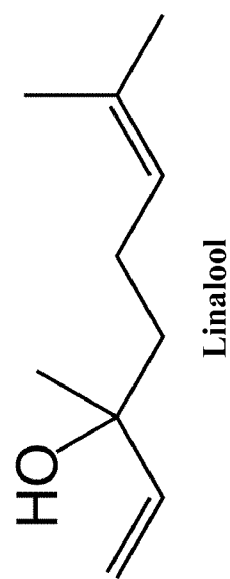
Figure 1:
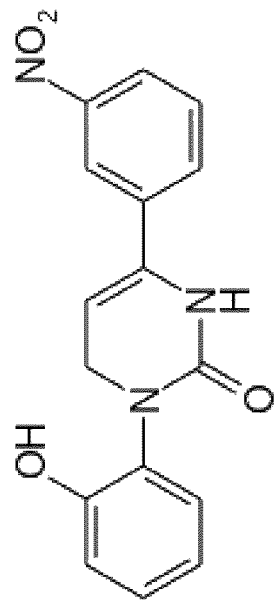

All percentages expressed herein are by weight of the total weight of the composition unless expressed otherwise. When reference is made to the pH, values correspond to pH measured at 25° C. with standard equipment. As used in this disclosure and the appended claims, the singular forms "a," "an" and "the" include plural referents unless the context clearly dictates otherwise. As used herein, "about" is understood to refer to numbers in a range of numerals. Moreover, all numerical ranges herein should be understood to include all integers, whole or fractions, within the range. The food composition disclosed herein may lack any element that is not specifically disclosed herein. Thus, "comprising" includes "consisting essentially of" and "consisting of."

As used herein, "autism disorder" includes, as non-limiting examples, classic autism, Asperger's syndrome, childhood disintegrative disorder, Rett syndrome, pervasive developmental disorders-not otherwise specified ("PDD-NOS"), and fragile X syndrome.

"Prevention" includes reduction of risk and/or severity of an autism disorder. The terms "treatment," "treat" and "to alleviate" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The term does not necessarily imply that a subject is treated until total recovery. The terms "treatment" and "treat" also refer to the maintenance and/or promotion of health in an individual not suffering from a disease but who may be susceptible to the development of an unhealthy condition. The terms "treatment," "treat" and "to alleviate" are also intended to include the potentiation or otherwise enhancement of one or more primary prophylactic or therapeutic measures. The terms "treatment," "treat" and "alleviate" are further intended to include the dietary management of a disease or condition or the dietary management for prophylaxis or prevention a disease or condition. A treatment can be patient- or doctor-related.

As used herein, a "therapeutically effective amount" is an amount that prevents a deficiency, treats a disease or medical condition in an individual or, more generally, reduces symptoms, manages progression of the diseases or provides a nutritional, physiological, or medical benefit to the individual.

"Animal" includes, but is not limited to, mammals, which includes but is not limited to, rodents, aquatic mammals, domestic animals such as dogs and cats, farm animals such as sheep, pigs, cows and horses, and humans. Where "animal," "mammal" or a plural thereof is used, these terms also apply to any animal that is capable of the effect exhibited or intended to be exhibited by the context of the passage. As used herein, the term "patient" is understood to include an animal, especially a mammal, and more especially a human that is receiving or intended to receive treatment, as treatment is herein defined. While the terms "individual" and "patient" are often used herein to refer to a human, the present disclosure is not so limited. Accordingly, the terms "individual" and "patient" refer to any animal, mammal or human, having or at risk for a medical condition that can benefit from the treatment.

As used herein, "infant" means a child under the age of 12 months. The expression "young child" means a child aged between one and three years, also called a toddler.

"Food product" and "food composition," as used herein, are understood to include any number of optional additional ingredients, including conventional food additives, for example one or more proteins, carbohydrates, fats, acidulants, thickeners, buffers or agents for pH adjustment, chelating agents, colorants, emulsifiers, excipients, flavor agents, minerals, osmotic agents, a pharmaceutically acceptable carrier, preservatives, stabilizers, sugars, sweeteners, texturizers and/or vitamins. The optional ingredients can be added in any suitable amount.

As set forth above, the present inventors surprisingly and unexpectedly found that several active compounds from spices can depress neural activity in neocortex and amygdale. These compounds are Menthol and Linanool which are transient receptor potential M8 (TRPM8) channel agonists. The present inventors discovered the same effect with Icilin, a synthetic super-agonist of the TRPM8 ion channel, even though the structure of Icilin is not related with Menthol; nevertheless, Icilin produces an extreme sensation of cold both in humans and animals. These natural compounds reduce neural excitability by 1) increasing the threshold to trigger an action potential and consequently increasing the amount of current required to trigger an action potential in the neocortex; and 2) abortion of action potentials at higher stimulation levels, most likely related to the use-dependent block of Na+ channels in the neocortex and lateral amygdale. These active compounds change the firing patterns especially at higher stimulation levels where a progressive and dramatic reduction of the action potential (APs) amplitude occurs until complete abortion of APs.

Without wishing to be bound by theory, the inventors believe that the mechanism underlying the selected active compounds of spices, namely Menthol, Linanool and Icilin, solves two main problems compared to glutamate antagonists: 1) Menthol, Linanool and Icilin target a presynaptic phase of APs, decreasing activity and diminishing glutamate release, which reduces drastically the possibility of reaching excitotoxicity levels; and 2) Menthol, Linanool and Icilin act stronger in the high stimulation context. In contrast to glutamate antagonists that typically inhibit the binding of glutamate to NMDA receptors, Menthol, Linanool and Icilin decrease neuronal activity, and target the pre-synaptic phase of the firing to reduce the possibilities of excitotoxicity one step earlier.

Accordingly, the composition provided by the present disclosure comprises a therapeutically effective amount of at least one of Menthol, Linalool or Icilin. In an embodiment, an autism disorder is treated or prevented by administering to an individual in need of same the composition comprising at least one of Menthol, Linalool or Icilin. For example, the composition comprising at least one of Menthol, Linalool or Icilin can be administered to an individual having an autism disorder to treat the autism disorder. The autism disorder can be classic autism, Asperger's syndrome, childhood disintegrative disorder, Rett syndrome, pervasive developmental disorders-not otherwise specified ("PDD-NOS"), fragile X syndrome, and combinations thereof. In an embodiment, the individual is an infant or a young child.

The composition comprising at least one of Menthol, Linalool or Icilin may be a medicament, a food product or a supplement to a food product. The supplement may be in the form of tablets, capsules, pastilles or a liquid, for example. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins or the like), adsorbents, carriers, fillers, co-compounds, dispersing agents, wetting agents, processing aids (solvents), flowing agents, taste masking agents, weighting agents, jellifying agents and gel forming agents. The supplement may also contain conventional pharmaceutical additives and adjuvants, excipients and diluents, including, but not limited to, water, gelatin of any origin, vegetable gums, ligninsulfonate, talc, sugars, starch, gum arabic, vegetable oils, polyalkylene glycols, flavoring agents, preservatives, stabilizers, emulsifying agents, buffers, lubricants, colorants, wetting agents, fillers, and the like.

The supplement can be added in a product acceptable to the consumer as an ingestible carrier or support. Non-limiting examples of such carriers or supports are a pharmaceutical, a food composition, and a pet food composition. Non-limiting examples for food and pet food compositions are milks, yogurts, curds, cheeses, fermented milks, milk-based fermented products, fermented cereal based products, milk-based powders, human milks, preterm formulas, infant formulas, oral supplements, and tube feedings.

In an embodiment, the composition comprising at least one of Menthol, Linalool or Icilin is administered to a human. The composition comprising at least one of Menthol, Linalool or Icilin is preferably intended for a consumption regime over an extended period of time, preferably over several years. For example, the composition can be administered periodically, such as weekly or daily, for at least one year, preferably at least two years, and more preferably even longer amounts of time.

Each of Menthol, Linalool and/or Icilin can be administered to the individual in a daily amount of 0.0015 mg/kg of body weight to 400 mg/kg of body weight, preferably 0.1 mg/kg of body weight to 300 mg/kg of body weight, more preferably 1.0 mg/kg of body weight to 200 mg/kg of body weight, and most preferably 10.0 mg/kg of body weight to 100 mg/kg of body weight. For example, the daily amount of each of Menthol, Linalool and/or Icilin administered to the individual can be 0.0015 mg/kg of body weight to 0.01 mg/kg of body weight, 0.01 mg/kg of body weight to 0.1 mg/kg of body weight, 0.1 mg/kg of body weight to 1.0 mg/kg of body weight, 1.0 mg/kg of body weight to 10.0 mg/kg of body weight, 10.0 mg/kg of body weight to 100.0 mg/kg of body weight, 100.0 mg/kg of body weight to 200.0 mg/kg of body weight, 200.0 mg/kg of body weight to 300.0 mg/kg of body weight, or 300.0 mg/kg of body weight to 400.0 mg/kg of body weight.

EXAMPLES

The following non-limiting examples present scientific data developing and supporting the concept of treatment or prevention of an autism disorder using Menthol, Linalool and Icilin.

A mouse brain slice was used to study the effects of Menthol, Linalool and Icilin. The amygdaloid complex is located within the medial temporal lobe in neocortex and amygdala. The lateral and basolateral nuclei of the amygdaloid complex receive sensory information from cortical and thalamic structures, process the information, and then transmit the information, either directly or through the basal nucleus, to the central nucleus. For experimental analysis of neural activity, synaptic responses from the basolateral complex can be evoked electrically using electrodes, and the action potentials can be measured.

Figure 2:
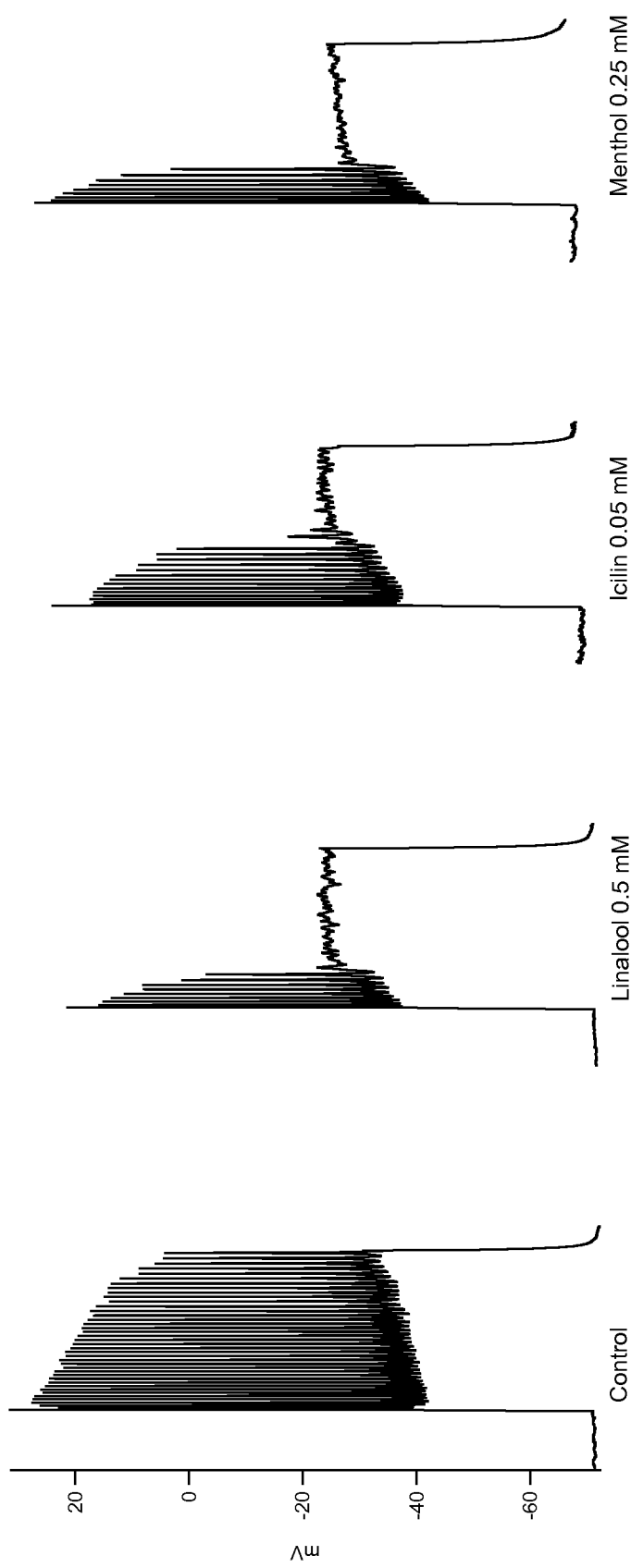
FIG. 2 shows charts of whole cell, current clamp recordings in a Lateral Amygdala glutamatergic neuron (in a mouse brain slice) in the absence (control) and presence of TRPM8 ligands Linalool, Icilin or Menthol.

FIG. 2 shows recordings in the absence of Menthol, Linalool or Icilin (control) and recordings in the presence of Menthol, Linalool or Icilin. A square pulse of 2.5 s was applied at high depolarization of membrane potential (approximately −30 mV). The recordings show that, in the presence of the TRPM8 ligands at high depolarization levels, inactivation of the sodium fast channels happens sooner relative to control, avoiding further neural firing.

Figure 3:
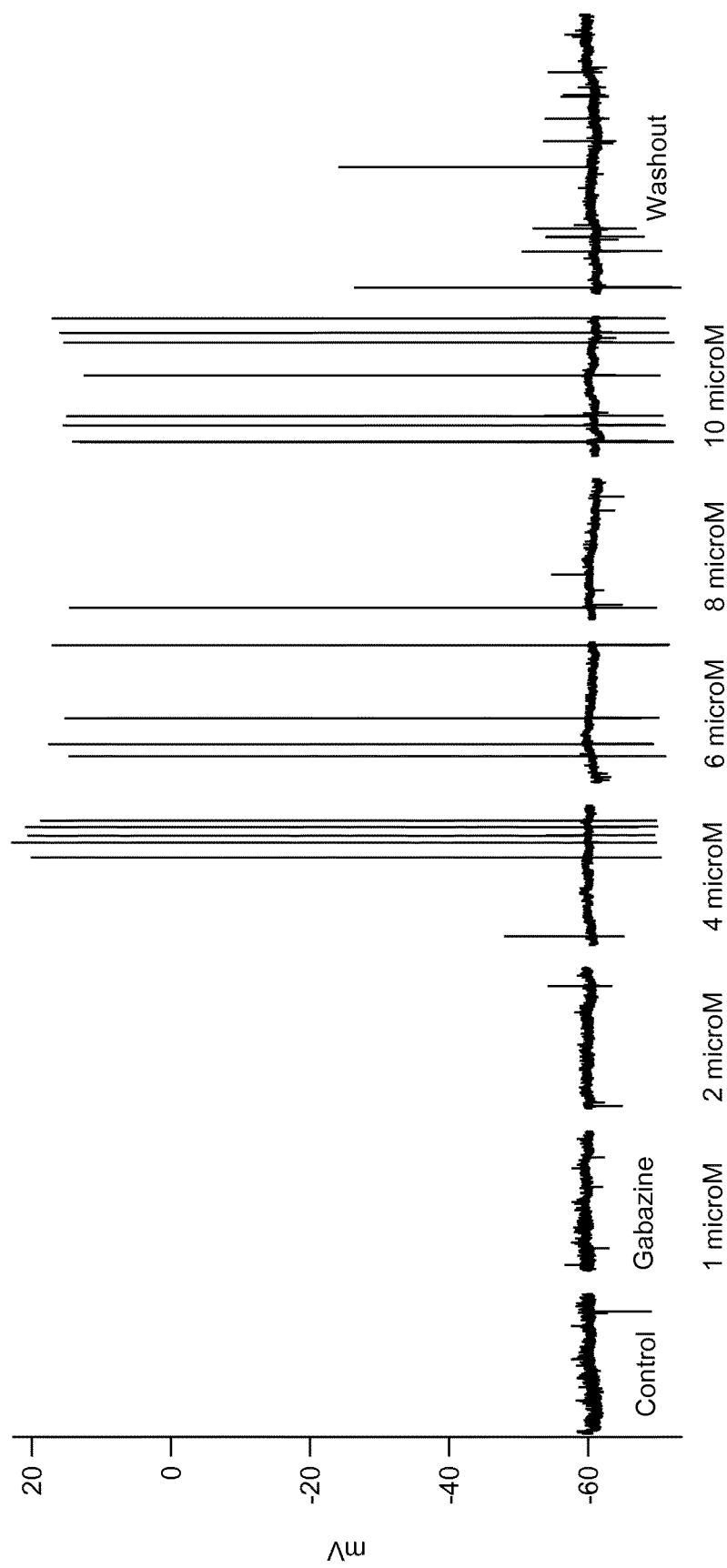
FIG. 3 shows a chart of whole cell, current clamp recordings in a Lateral Amygdala glutamatergic neuron (in a mouse brain slice) with increasing concentration of gabazine (GABA A blocker) applied extracellularly during recordings of 5 min each (washout 10 min).
Figure 4:
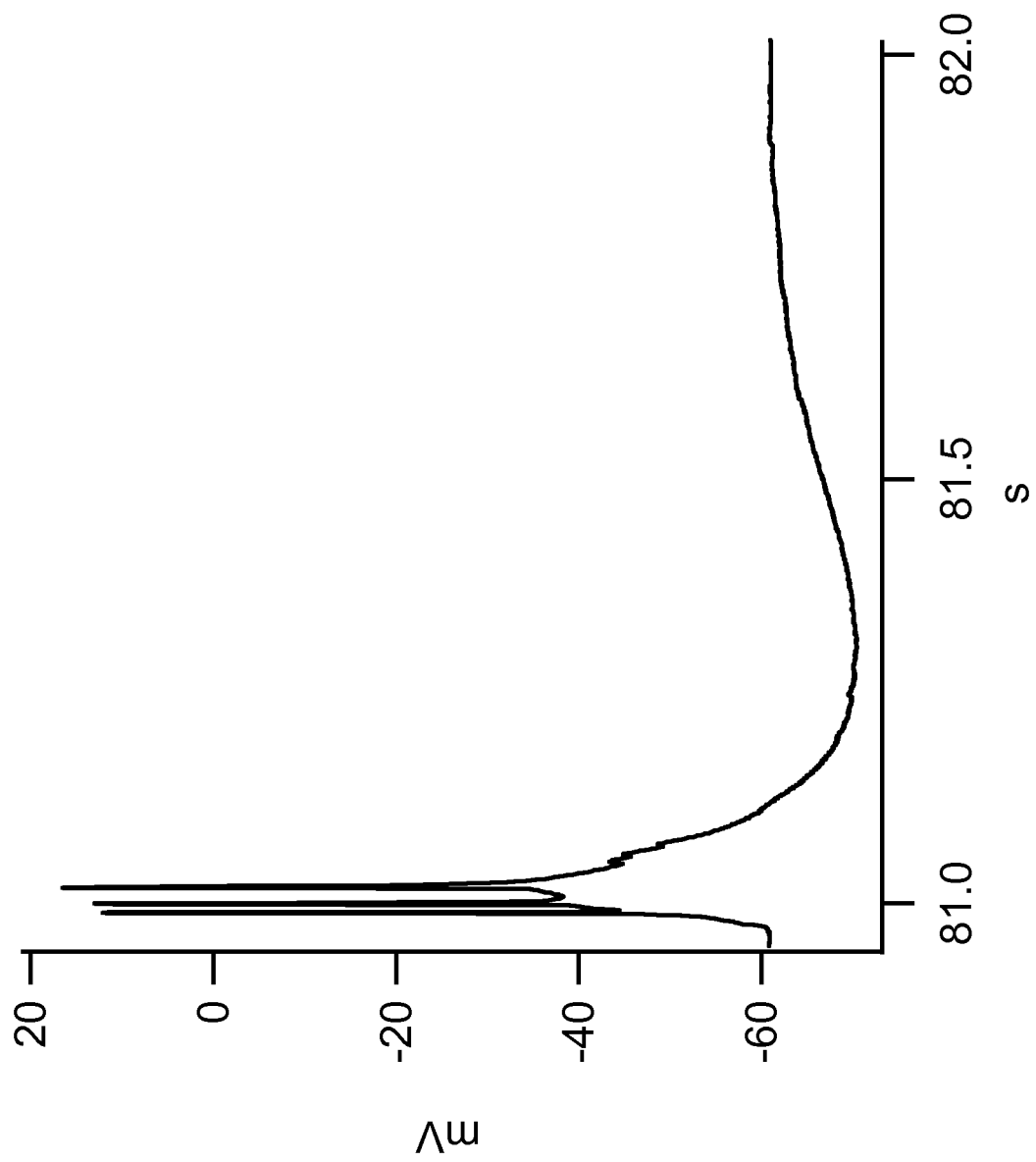
FIG. 4 shows a chart of whole cell, current clamp recordings in a Lateral Amygdala glutamatergic neuron (in a mouse brain slice) showing enhanced detail of a burst.
Figure 5:
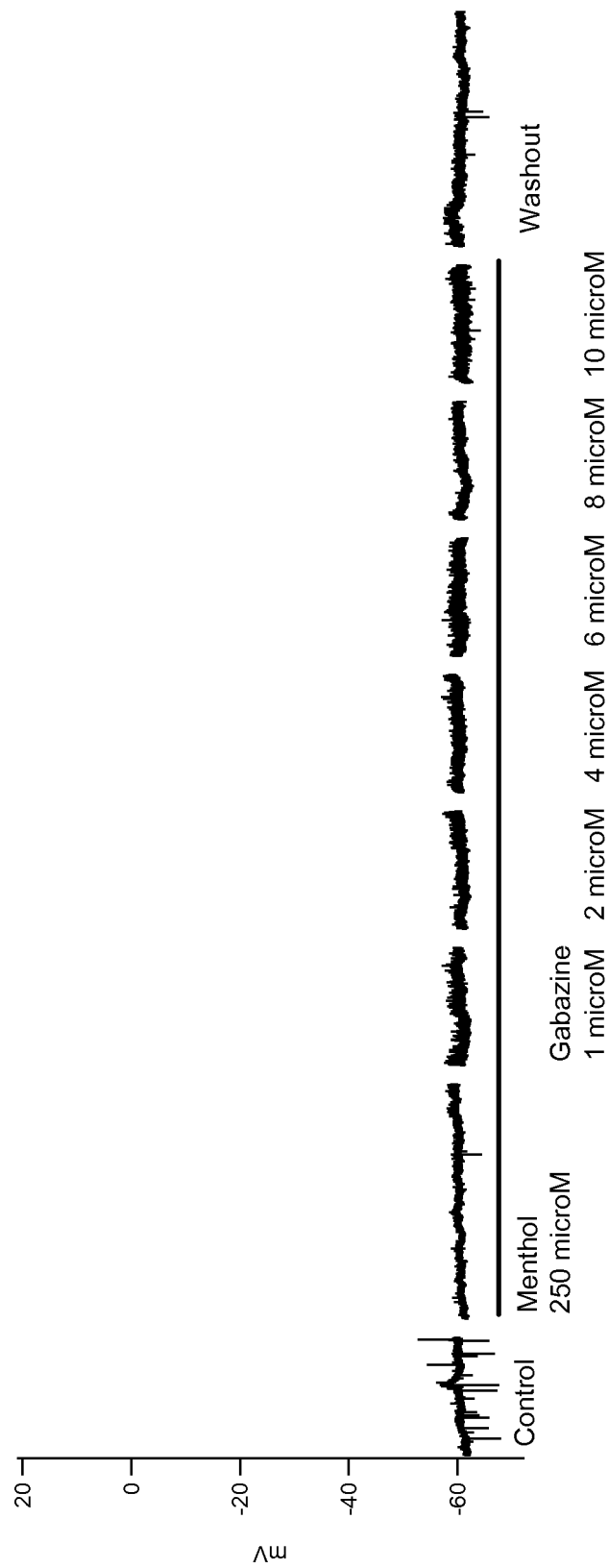
FIG. 5 shows a chart of whole cell, current clamp recordings in a Lateral Amygdala glutamatergic neuron (in a mouse brain slice) with increasing concentration of gabazine (GABA A blocker) applied extracellularly during recordings of 5 min each (washout 10 min.) while 10 minutes previous to and during the exposure of the different concentrations of gabazine, 250 µM menthol was also applied extracellularly.

FIG. 3 shows recordings in increasing concentrations of gabazine, a GABA A blocker, applied extracellularly during recordings of 5 minutes each with 10 minute washout. As shown, neurons spontaneously present action potential bursts due to massive presynaptic discharges. FIG. 4 depicts enhanced detail of one of the bursts and shows that serial action potentials can be observed in a single burst. For comparison to FIG. 3, FIG. 5 shows recordings under the same conditions, namely increasing concentrations of gabazine applied extracellularly during recordings of 5 minutes each with 10 minute washout, except that in FIG. 5, Menthol 250 µM was applied extracellularly at 10 minutes previous to and during the exposure of the different concentrations of gabazine. As illustrated in the figure, neurons show a complete absence or a strongly decreased presence of spontaneous bursts (compare FIG. 5 to FIG. 3).

These experimental results demonstrate that Menthol, Linalool and Icilin increase the threshold to trigger an action potential and consequently increase the amount of current required to trigger an action potential in the neocortex, and also abort action potentials at higher stimulation levels.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method for treating an autism disorder comprising administering to an individual having the autism disorder a composition comprising Menthol, and the composition is administered daily in an amount that provides a daily dose of the Menthol from 10.0 mg/kg of body weight of the individual to 100.0 mg/kg of body weight of the individual.

2. The method of claim 1 wherein the autism disorder is selected from the group consisting of classic autism, Asperger's syndrome, childhood disintegrative disorder, Rett syndrome, pervasive developmental disorders-not otherwise specified, fragile X syndrome, and combinations thereof.

3. The method of claim 1 wherein the composition is selected from the group consisting of a medicament, a food product and a supplement to a food product.

4. The method of claim 1 wherein the composition is administered daily for at least one year.

5. The method of claim 1 wherein the individual is an infant.

6. The method of claim 1 wherein the individual is a young child.

7. The method of claim 1 wherein the composition is administered for at least two years.

8. The method of claim 1 wherein the composition further comprises protective hydrocolloids.

9. The method of claim 1 wherein the composition is a food product.

10. The method of claim 9 wherein the food product comprises a component selected from the group consisting of protein, carbohydrate, fat and combinations thereof.

11. The method of claim 1 wherein the composition does not contain glutamate antagonists.

12. The method of claim 1 wherein the composition is a food product consisting of the Menthol and optionally one or more components selected from the group consisting of protein, carbohydrate, fat, an acidulant, a thickener, a buffer, a pH adjustment agent, a chelating agent, a colorant, an emulsifier, an excipient, a flavor agent, a mineral, an osmotic agent, a pharmaceutically acceptable carrier, a preservative, a stabilizer, a sugar, a sweetener, a texturizer and a vitamin.

13. The method of claim 1 wherein the composition is a food supplement consisting of the Menthol and optionally one or more components selected from the group consisting of a gum, a protein, a modified starch, a binder, a film forming agent, an encapsulating agent, a wall or shell material, a matrix compound, a coating, an emulsifier, a surface active agent, an oil, a fat, a wax, lecithin, an adsorbent, a carrier, a filler, a co-compound, a dispersing agent, a wetting agent, a solvents, a flowing agent, a taste masking agent, a weighting agent, a jellifying agent, and a gel forming agent.

* * * * *